United States Patent [19]

Whitesides et al.

[11] 3,950,135
[45] Apr. 13, 1976

[54] METHOD OF SEPCTRAL ANALYSIS USING NMR SHIFT REAGENTS

[75] Inventors: George M. Whitesides, Newton, Mass.; Michael McCreary, Rochester; Daniel Lewis, Support Command, APO, both of N.Y.

[73] Assignee: Massachusetts Institute of Technology, Cambridge, Mass.

[22] Filed: July 24, 1974

[21] Appl. No.: 491,594

[52] U.S. Cl............ 23/230 R; 23/230 M; 260/429.2
[51] Int. Cl.²..................... C01F 17/00; G01N 27/78
[58] Field of Search................ 23/230 R; 260/429.2

[56] References Cited
UNITED STATES PATENTS

| | | | |
|---|---|---|---|
| 3,700,410 | 10/1972 | Sievers | 23/230 R |
| 3,789,060 | 1/1974 | Goering | 260/429.2 |
| 3,846,333 | 11/1974 | Sievers | 260/429.2 |
| 3,867,418 | 2/1975 | Burgett | 260/429.2 |

OTHER PUBLICATIONS

M. D. McCreary et al., J.A.C.S., 96, 1038–1054, (Feb. 20, 1974).

*Primary Examiner*—Joseph Scovronek
*Assistant Examiner*—Sidney Marantz
*Attorney, Agent, or Firm*—Arthur A. Smith, Jr.; David G. Conlin; Martin M. Santa

[57] ABSTRACT

The ability of nuclear magnetic resonance spectroscopy to distinguish between compounds and between parts of compounds is substantially increased by the use of certain rare earth chelate shift reagents. The preferred shift reagents are the europium III chelates of substituted or unsubstituted dicampholyl ligands, and europium III chelates of substituted or unsubstituted nopinato compounds. The reagents are particularly useful in determining the enantiomeric purity of compositions containing mixtures of enantiomers.

9 Claims, No Drawings

METHOD OF SEPCTRAL ANALYSIS USING NMR SHIFT REAGENTS

The invention herein described was made in the course of work performed under a grant from the National Institute of Health.

BACKGROUND

This invention relates to special analysis of organic compounds by nuclear magnetic resonance spectroscopy (NMR), and to compositions which facilitate the interpretation of a compound's NMR spectrum. One aspect of the invention particularly concerns the use of NMR techniques in determining the enantiomeric purity of chiral organic substances, using particular shift reagents which are effective in inducing chemical shifts between corresponding resonances of the enantiomeric materials.

NMR spectroscopy has been used for many years in the identification of compounds by comparing the spectra of known compounds with those of the compounds to be analyzed and by providng magnetic parameters (chemical shifts and coupling constants) that have been found to be characteristic of particular types of structures. The techniques employed in this method of spectral analysis are described in the literature, and NMR spectrometers are commercially available. Briefly, in the operation of a spectrometer, a tube containing a sample to be analyzed is positiond between the pole faces of an electromagnet. An oscillating radio frequency field is imposed at right angles to the external magnetic field. A radio frequency receiver detects the magnetic moment induced in the sample 90° out of phase from the radio frequency field. When nuclear transitions or resonances are induced, energy is absorbed from the receiver, and the voltage across the receiver coil changes. After this voltage change is amplified and detected, the resulting direct current voltage is displayed on an oscilloscope or X-Y recorder. The NMR spectrum, a pattern of intensity as a function of frequency, is thereby produced. An interpretation of the spectrum makes it possible to determine the presence of certain nuclei contained in molecules (particularly $^1H$, $^{13}C$, $^{19}F$, $^{31}P$, $^{11}B$) and their relationship to one aother and the the remainder of the molecule, and thereby to infer the structure of the molecule or of parts of the molecule.

Conditions for resonances are expressed in terms of chemical shifts ($\delta$) or differences between the fields necessary for resonance in the sample and an arbitrarily chosen reference material, usually tetramethylsilane (TMS) for proton resonance, and in terms of nuclear spin — spin coupling constants, $J$, which characterize the interactions between the various magnetic nuclei. Samples to be subjected to nuclear magnetic resonance conventionally contain a reference material having only a single resonance line, which serves to locate the resonant frequency of a sample in a magnetic field. Examples of typical reference compounds include tetramethylsilane, chloroform, cyclohexane and benzene.

Since the beginning of NMR spectroscopy in the late 1940's the effects of paramagnetism on nuclear magnetic resonances have been the object of considerable study. One goal of these studies has been to provide means to simplify and clarify the NMR spectrum, thereby rendering compound identification more certain, as well as increasing the scope of the applicability of NMR spectroscopy. As a result, so-called shift reagents have been developed, which, when added to a sample of a compound subjected to NMR, will cause frequency shifts that desirably will result in a high resolution spectrum without objectionable broadening overlap of the peaks which are displayed on the oscilloscope or graph when resonances occur. A number of such shift reagents have been reported. See e.g., U.S. Pat. No. 3,700,410 issued Oct. 24, 1972, to R. E. Sievers, incorporated herein by reference; *J. J. American Chemical Society*, 91: 5160 (1969) and *Chem. Commun.*, 422 (1970).

One of the most difficult problems in analytical chemistry has been the determination of the enantiomeric purities of chiral substances. Enantiomers are chemical compounds which are mirror images of each other. Compounds that are capable of being resolved into mirror form (e.g. into enantiomers) are chiral. Enantiomeric compounds have identical chemical properties, except for the direction in which they rotate plane polarized light, and except toward optically active reagents. Because of the similarity in their properties, analysis for the relative amounts of different enantiomers has traditionally been difficult, and the classical methods for this determination are experimentally cumbersome.

A number of attempts have been made to devise ways in which the more convenient techniques of NMR spectroscopy could be used to analyze enantiomer-containing substances, e.g. to determine the optical purity of such materials. However since enantiomeric molecules have the chemical composition, the resolution of differences between two enantiomers is probably one of the most difficult tasks yet assigned to nuclear magnetic resonance spectroscopy. The molecular difference between different enantiomers is only the difference in the arrangement of the components of the molecules in space, e.g., around an asymmeteric carbon atom, such as for the simple sec-butyl alcohol enantiomers illustrated below:

The previous NMR techniques included the use of optically active solvents, which interact differently to some degree with the optically active sample. However, the applicability of NMR procedures based on diasteriomeric interactions between enantiomer solutes and optically active solvents is limited by the small magnitude of chemical shift differences induced between corresponding resonances of enantiomers. Other techniques included the reaction of the sample to form more complex diasteriomeric compounds, e.g. diasteriomeric fluorine 19-containing esters, and the use of known shift reagents.

It has previously been demonstrated that certain NMR shift reagents composed of tris chelates of chiral $\beta$-diketone ligands with europium(III), shift corresponding resonances of many enantiomeric organic substances to different extents. See, e.g. Whitesides et al., *J. Amer. Chem. Soc.* 92: 6979 (1970), Goering et al., *J. Amer. Chem. Soc.* 93: 5913 (1971), Whitesides et al., *J. Amer. Chem. Soc.* 93: 5914 (1971), and Fraser et al., *Chem. Commun.* 1450 (1971), all incorporated herein by reference. Where the shift reagents can be used for this purpose they have a number of advantages over the previously used methods of determining enantiomeric purity, such as NMR spectroscopy of enantiomeric mixtures in optically active solvents, or NMR spectroscopy of diasteriomeric fluorine 19 containing esters. The use of the shift reagents is a far more convenient experimental procedure than previous ones, and gives spectra which are much easier to interpret. No chemical manipulation of the sample is required with the use of shift reagents, i.e. the reagents themselves do not react irreversibly with the sample. Moreover, even the less readily prepared of the chiral shift reagents are more easily obtained than the necessary quantities of the useful optically active solvents previously used. Most importantly, both the enantiomeric shift differences ($\Delta\Delta\delta$), i.e. the differences in NMR spectra obtained between enantiomers and the chemical shifts ($\Delta$) obtained using chiral shift reagents are usually larger than the corresponding parameters obtained in the other NMR methods. Thus it is possible to carry out a quantitative determination of the enantiomeric composition of structures having sufficient complexity that analysis of their unshifted spectrum would be difficult.

However a number of problems exist with regard to those shift reagents previously known and used for this purpose. Some shift reagents were usable with only a limited number of enantiomeric compounds such as strongly basic amines and the like. Less strongly basic enantiomers could not be resolved or received only minimal resolution by use of the reagents.

It is therefore an object of this invention to provide an improved method of NMR spectral analysis. Another object is to provide shift reagents that can be effectively used with a wide variety of compounds having diverse substituent groups. Another object is to provide shift reagents which are effective in inducing chemical shifts between corresponding resonances of enantiomeric materials without objectionable peak broadening. Another object of the invention is to provide shift reagents which give high resolution spectra for wide varieties of compounds. Still another object of the invention is to provide a method of analysis for enantiomeric compounds which is relatively simple, which takes advantage of the NMR technique, and which does not suffer from many of the advantages of previously known techniques. A still further object of the invention is to provide shift reagents which are particularly useful in determinations of enantiomeric purity.

Other objects and advantages of the present invention will become apparent to those skilled in the art upon a consideration of the present disclosure or upon making or using the invention disclosed herein.

Basically the invention involves use of improved shift reagents in NMR spectroscopy. The preferred reagents for the purposes of this invention are the rare earth chelates of substituted or unsubstituted dicampholyl ligands. Of these, the most preferred are the tris [d,d-dicampholythmethanato] and tris [1,1-dicampholylmethanato] chelates, preferably the europium chelates.

Other novel shift reagents which are particularly useful for the analysis of a number of optically active isomers are the substituted and unsubstituted nopinato compounds of the following formula:

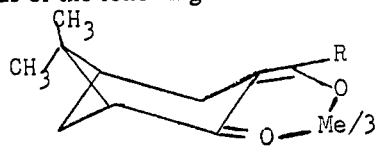

Wherein R is an organic group which is not extremely bulky, which is not base sensitive, and which does not itself contain basic groups. Normally R should contain no carbonyl or ester groups, or allylic unsatuation. R may be aryl or alkyl and preferably is either unsubstituted or halogenated. Preferably R is lower alkyl or halogenated lower alkyl of 1 to 10 carbon atoms. Me in the above formula stands for the paramagnetic trivalent rare earth ions, i.e., cerium, prasodymium, neodymium, samarium, europium, gadolinium, terbium, dysposium, holmium, erbium, thulium, or ytterbium. Again, the preferred chelate is europium (Eu).

The preferred dicampholyl shift reagents have shown substantial improvement over previously known shift reagents both in the shift differences induced and in the variety of compounds for which substantial shift differences can be induced. These differences constitute the distances between peaks in the NMR spectra of the corresponding atomic components of the compounds in the sample. Without desiring to be bound by theory, such differences obtained by use of shift reagents are believed to be due to differences in the stability constants for diasteriomeric complexes formed between the enantiomers and the shift reagents, and to differences in the geometrics of the diasteriomeric complexes thus formed. The larger the enantiomeric shift differences ($\Delta\Delta\delta$), the easier it is to analyze the spectra of a sample for enantiomeric purity. Generally, shift differences below about 0.01 parts per million on an NMR spectrum are too small to be observable, and shift differences of above 0.1 ppm are preferred. However, analysis with shift reagents which provide even as low 0.02 ppm separation may be useful where the alternative methods of enantiomer analysis are extremely cumbersome or, in some cases not workable.

The preferred dicampholyl shift reagents of the present invention give consistently measurable shift differences for the various molecules components of a wide variety of optically active compounds. As shown in the example below, tris [d,d-dicampholylmethanato] europium (III) (Eu (dcm)$_3$), gave useful shift differences for components of a comparatively wide variety of compounds, and gave a shift difference as high as 4.42 ppm (for the tertiary hydrogen in 1-phenylethylamine).

The nopinato shift reagents of the present invention, although neither generally as effective nor as broad in application as the preferred dicampholyl reagents, do show some advantages, even over those reagents, for certain enantiomers. See, e.g. the results reported for N, N-dimethyl -1- phenylethylamine in the examples below. The nopinato shift reagents give results which are superior to those obtained from previously known shift reagents for certain hard-to-analyze enantiomers. Also, the nopinato shift reagents are generally easier to prepare than the dicampholyl reagents.

In practicing the invention, the sample to be analyzed is mixed with the shift reagent of the invention in a non-basic solvent in which both are soluble. Even weakly basis solvents are capable of tying up the europium and lowering the observed chemical and enantiomeric shifts. Any sequence of mixing is effective, and both, either, or neither of the shift reagent and the sample may be in the solvent prior to mixing. Any non-interfering solvent can be used, preferably hydrocarbons such as pentane, 1,1,2-trichloro-1,1,2-trifluoroethane, chloroform, deuterated chloroform, and carbon tetrachloride, and also carbon disulfide, fluorotrichloromethane, benzene, methylene chloride, and others known in the art. As noted above, the sample to be analyzed should contain an NMR reference compound in order to standardize the test. Known reference compounds such as tetramethylsilane, chloroform, cyclohexane and benzene are useful in accordance with the present invention. The solvent used may partially or totally perform the function of the reference material. Mixtures of solvents may also be used, provided that neither exhibit resonance in the region of the sample spectrum.

The amount of shift reagent present in the final sample may range from about 0.01 to about 1.0 mole per liter, preferably from about 0.1 to 0.8 mole per liter. Optimum results appear to be obtained with a concentration of from about 0.2 to 0.4 or 0.5 moles per liter. The amount of sample may range from about 0.05 moles per liter to about 1 mole per liter, preferably 0.1 to 0.5 moles per liter depending on the solvent used, limitations of the solubility of either the shift reagent or the sample or both. Where one is extremely soluble in the system, it tends to aid in solubilizing the other. Where a separate reference compound is used, it may be present in a range of from about 0.05 to about 2% be weight preferably about 0.1 to 1% by weight in the solution.

Spectral shifts take place over wide ranges of temperature, e.g. from as high as 200° C or above to as low as below −100°C. The shift reagents generally give greater enantiomeric shift differences at lower temperatures, and thus spectra that are more easy to interpret. The preferred temperature range is from about +40°C to about −75°C, most preferably between about +25°C and −50°C. The solubilities of shift reagent and sample in a given solvent generally go down and the widths of lines may increase with lower temperatures, and thus phase separation and spectral resolution difficulties may ensue if too low temperatures are attempted. Again, where one solute is very soluble in the solvent it may act to a degree as cosolvent for the other solute and thus improve its solubility in the system.

While chemical modifications is often unnecessary to produce good spectra using the reagents of the present invention, it to may be resorted to in order to place more easily analyzable groups on compounds which are difficult to analyze. For example, citronellol, which is extremely difficult to determine by NMR techniques, can be converted to the more easily examinable acetate, trifluoroacetate, pivalate or 3,3-dimethylbutanoate compounds, or other compounds which will be apparent to the skilled artisan. Also, sample compounds which adversely react under test conditions, such as carboxylic acids which decompose europium chelates, may be converted to less reactive compounds, e.g. alkyl esters, prior to analysis.

Both the dicampholyl and the nopinato shift reagents can be prepared by condensation of the enolate anion of the appropriate alkyl ketone with the appropriate carboxylic acid chloride or ester. For example the dicampholyl shift reagents may be prepared from campholic acid, which can be prepared from camphor by known methods, by converting the acid into the acid chloride, and converting other campholic acid into the alkyl, e.g. methyl, ketone. The ketone is converted into the enolate anion and then is reacted with the campholyl acid chloride to produce the dicampholymethanato ligand. The choice of the base utilized in forming the enolate of the intermediate alkyl ketone is important: the use of sodium hydride or sodium amide requires vigorous reaction conditions, but substitution of lithium diisopropylamide for these bases results in fewer self condensation products and less acylation and permits the enolization reaction to be carried out under mild conditions.

The conversion of the dicampholylmethanato and the nopinato ligands into rare earth chelates may be accomplished by treating the ligand first with sodium hydroxide in aqueous methanol and then with a rare earth salt, e.g. europium trichloride hexahydrate or by other methods known in the art. A more detailed description of the preparation of these compounds can be found in McCreary et al, Determination of Enantiomeric Purity Using Chiral Anthanide Shift reagents *J. Amer. Chem. Soc.* 96: 1038–54 (1974), incorporated herein by reference, and is shown in the samples below. The shift reagents in accordance with this invention are thermally stable, oxygen-insensitive glasses or solids which have good solubility in organic solvents. They are decomposed by acids and by materials capable of chelating with the europium ion, e.g., alpha-diketones, or alpha-dioximes.

EXAMPLE 1

Preparation of tris[d,d-dicampholylmethanato] europium(III)

A mixture of d-camphor (404 g, 2.66 mol) and potassium hydroxide pellets (809 g, 14 mol) was heated in a 3 liter rocking steel bomb at 245° for 24 hours. The bomb was cooled and the solid was removed with steam and hot water. The aqueous solution was filtered through Celite with suction while warm, washed with two 1.5 liter portions of ether, made acidic with concentrated hydrochloric acid, and extracted with six 1.5 liter portions of ether. The combined organic layers were dried and concentrated. Distillation of the resulting crude yellow solid through a short Vigreux column yielded a pale yellow wax (bp 120°–127°, 2.2 Torr), which was recrystallized twice from pentane to give 226 g of a white crystalline solid (d-campholic acid): mp 92° – 100°; $[\alpha]^{25}$ D +45.4° (c 2.5, $C_2H_5OH$) ir 1690 (C=O) and 2300–3400 $cm^{-1}$ (C—H and OH) nmr 0.76, 1.04, and 1.24 (s, 3 each, $CCH_3$), 0.89 (d, 3, J + 6.0 Hz, $CHCH_3$), 11.84 (s, 1, $COOH$), and 0.6–2.8 (m).

To a flame-dried, nitrogen-purged, 500-ml, round-bottomed flask fitted with reflux condenser, magnetic stirring bar and calcium chloride drying tube was added 60.0 g (0.35 mol) of d-campholic acid, 64 ml of thionyl chloride (2.5 fold excess), and 200 ml of dry benzene. The mixture was stirred vigorously while refluxing for 16 hours. The reaction mixture was concentrated at reduced pressure, and the resulting yellow oil was distilled to give 60.0 g of d-campholyl chloride as a colorless liquid: bp 94° (12 Torr); ir 1790 $cm^{-1}$ (C=O); nmr 0.82, 1.11. and 1.34 (s, 3 each, $CCH_3$), 0.90 (d, 3, J = 6.4 Hz, $CHCH_3$), and 1.4–2.8 (m).

d-Campholic acid (131 g., 0.771 mol) was dissolved in 700 ml. of freshly distilled 1,2-dimethoxymethane in a flame-dried, nitrogen-purged, 3-liter flask equipped with a mechanical stirrer and a reflux condenser. An atmosphere of prepurified nitrogen was maintained in the reaction apparatus throughout the reaction. A 1.6 M solution of methyllithium in ether (1.00 liter) was allowed to drip into the reaction mixture at a rate that sustained a gentle reflux (ca. 1 liter per 1.5 hr.). Methane was evolved during the addition of the first equivalent of methyllithium. After refluxing and stirring for 18 hours, the cloudy white reaction mixture was transferred via cannula into 3 liters of well stirred water. The aqueous phase was extracted with three liter portions of ether, and the combined organic phase was washed with 700 ml of water, dried, and concentrated. Distillation afforded 85.6 g of the ketone (d-campholyl methane) as a colorless liquid: bp 94°–96° (13.5 Torr); $[\alpha]^{25}$ D +59.5°(c 10.0, $CCl_4$); ir 1700 $cm^{-1}$ (C=O); nmrδ 0.61, 1.06, and 1.14 (s, 3 each, $CCH_3$), 0.85 (d, 2, J = 7.0 Hz, $CHCH_3$), 2.05 (S, 3, $COCH_3$) and 0.6–2.8 (m). Anal. calculated for $C_{11}H_{20}O$: C, 78.51; H, 11.98. Found C, 78.58; H, 12.01.

To a flame-dried, nitrogen-purged, 2 liter round-bottomed flask equipped with a mechanical stirrer, nitrogen inlet, and low temperature thermometer was added a crystal of 2.2'-bipyridyl indicator and 380 ml (0.615 mol) of 1.62 M methyllithium in ether. The solution was cooled to −20° and 62.3 g (0.615 mol) of diisopropylamine was added via syringe. Gas was evolved and the solution changed in color from red-orange to orange. After stirring the lithium diisopropylamide for 30 minutes at −20°, 103.6 grams of d-campholylmethane (0.616 mol), dissolved in 100 ml of freshly distilled ether and cooled to −20° were rapidly added to the reaction solution via cannula. The enolate solution (now more intensely orange) was stirred at −20° for 25 minutes and was then cooled to −60°.

d-Campholyl chloride (116 g, 0.615 mol) was dissolved in 50 ml of freshly distilled ether, cooled to −60° and added to the enolate via cannula as rapidly as possible. After stirring at −50° to −70° for 30 minutes, the reaction mixture as warmed to −20° over a period of 30 minutes and was transferred via cannula into a well-stirred mixture of 1 M hydrochloric acid (1.2 liter) and ice. The aqueous phase (acidic to pH paper) was extracted with four 1.2 liter portions of ether, and the combined organic phase was washed with two 1 liter portions of sodium chloride solution, dried and concentrated. Distillation of the crude red oil gave a white, opaque paste (bp 100°–118°, ca. 0.06 Torr). Two recrystallizations from methanol/ethanol gave 69.2 g of the diketone d,d-dicampholylmethane (H(dcm)) as a white crystalline solid; mp 64.5°–65.0°; $[\alpha]^{25}$ D +88.9° (c 0.62, $C_2H_5OH$); ir 1790 (C=O) and 1720 $cm^{-1}$ (C=O); nmrδ 0.61, 1.03, and 1.15 (s, 6 each, $CCH_3$), 0.85 (d, 6, J = 7.2 Hz, $CHCH_3$), 5.60 (s, 1, vinyl $H$) 16.90 (s, 1, $OH$), and 0.6–2.7 (m). Anal. Calculated for $C_{12}H_{36}O_2$: C, 78.69; H, 11.32. Found: C, 78.48; H, 11.22.

d,d-Dicampholylmethane (25.9 g, 0.081 mol) was dissolved in 600 ml of a reagent grade methanol (40°) in a nitrogen-purged round-bottomed, flask equipped with a mechanical stirrer and nitrogen inlet. Synthesis of lanthanide chelates carried out under nitrogen lead to higher yields and purity than those carried out without excluding air, presumably by preventing oxidation of the β-diketone ligands. Magnetic stirrers are conveniently used for this reaction on a smaller scale. A solution of 4.37 g (0.081 mol) of sodium methoxide in 50 ml methanol was added, and the solution was stirred for several minutes. Upon addition of a filtered solution of 9.89 g (0.027 mol) of europium (III) chloride hexahydrate in 200 ml of methanol a cream-white precipitate immediately formed. The suspension was stirred vigorously for two hours, cooled to 0°, and filtered with suction to give several brittle beige lumps and a cream-colored amorphous solid. The product was dissolved in pentane, filtered to remove the insoluble material, concentrated, and dried at 100° (0.1 Torr) for 36 hours to give 18.8 g of tris [d,d-dicampholylmethanato] europium(III) as a white powder: mp 222.0°–227.5°; $[\alpha]^{25}$ D +28.6° (c 5.4, $CCl_4$); $^{56}$ ir 1540 $cm^{-1}$; nmrδ (broad) −0.02; 0.09, and 3.63 (s, 3 each, $CH_3$), and 1.10 (d, 3, J = $H_z$, $CHCH_3$). Anal. Calculated for $C_{63}H_{105}EuO_6$: C, 68.14; H, 8.94. Found: C, 67.86; H, 9.38.

EXAMPLE 2

Tris [1,1-dicampholylmethanato] europium(III) may be prepared following the steps of Example 1, but usng 1-camphor or 1-camphoric acid as a starting material.

EXAMPLE 3

Tris [d,d-dicampholylmethanato] holmium(III) may be prepared from d,d-dicampholylmethane in the same manner as the last step of Example 1, albeit substituting 0.027 moles of holmium trichloride hexahydrate for the 0.027 moles of europium chloride hexahydrate.

EXAMPLE 3A

Tris [d,d-dicampholylmethanato] praseodymium-(III) can be prepared in the same manner as the last step of Example 1, substituting 0.027 moles of praseodymium trichloride heptahydrate for the 0.027 moles of europium chloride hexahydrate.

EXAMPLE 4

Preparation of tris[3-trifluoroacetyl - d-nopinato] europium(III).

A solution of 80 g (0.59 mol) of 1-β-pinene in 720 ml of absolute methanol was ozonized according to the procedure of Meinwald et al., *J. Amer. Chem. Soc.* 82:5445 (1960). After workup and distillation, 60 g (73%) of the ketone d-nopinone was isolated as a colorless oil: bp 86°–88° (10 Torr); $[\alpha]^{25}$ D =16.9° (neat); ir 1710 $cm^{-1}$ (C=O); nmrδ 1.4–2.8 (m, 8), 1.35 (s, 3, $CH_3$), and 1.85 (s, 3, $CH_2$).

d-Nopinone, 13.8 g. (0.10 mol) allowed to react with 0.1 mole of lithium diisopropylamide prepared in accordance with Example 1, to form the enolate, which was then reacted with 14.2 grams (0.10 mol) of ethyl trifluoroacetate. The crude reaction mixture was quenched in 250 ml of cold 1 M hydrochloric acid, and the aqueous phase was extracted with four 175 ml portions of ether. The combined organic phase was washed with two 50 ml portions of saturated aqueous sodium chloride solution, and then extracted with two 50 ml portions of cold 1 M sodium hydroxide. The combined basic extracts were made acidic with 1 M hydrochloric acid and extracted with three 100 ml portions of ether. The combined ethereal layers were washed with saturated aqueous sodium chloride, dried, concentrated and distilled to give 8.9 g of the pure ketone 3-trifluoroacetyl -d-nopinone as a colorless liquid: bp 68° (2.5 Torr); $[\alpha]^{24}$ D +21.7° (neat), $[\alpha]^{24}$ D +12.9° (c 2.0, $CCl_4$); ir 1790, 1720, 1650 (strong), and 1720 $cm^{-1}$; and nmrδ 0.95 and 140 (s, 3 each, $CH_3$), 2.2–3.0 (m), and 14.8 (s, broad, 1 $OH$).

The 3-trifluoroacetyl -d-nopinone was converted to tris [3-trifluoroacetyl -d-nopinato] europium(III) by treating 17.5 grams of it with a equimolar amount of sodium methoxide in methanol as in Example 1. After the europium (III) chloride hexahydrate was added, the reaction mixture was stirred for one hour, 200 ml of water was added, and then the product was extracted from the resulting oily mixture with three 150 ml portions of pentane. The combined organic layers were washed with water, concentrated, dried for 36 hours at 100°C (0.1 Torr), and powdered to give 18.2 grams of tris [3-trifluoroacetyl -d-nopinato] europium(III) as a bright yellow amorphous solid: m.p. 80°–100°; $[\alpha]^{24}$ D −67.2° (c 2.0, $CCl_4$); ir 1600 – 1660 $cm^{-1}$; nmrδ 0.6 – 3.0 (s, broad).

As will be well understood in the art, other substituents than trifluoro methyl at the three position may be prepared by using acylating agents other than ethyl trifluoroacetate. Aryl and substituted aryl compounds, for example, may be prepared by acylation with the corresponding benzoate. Alkyl groups or substituted alkyl groups, such as halogenated alkyl groups, can be substituted for the trifluormethyl group by using the corresponding esters. Suitable esters include acetates (for $-CH_3$) propionate (for $-CH_2-CH_3$), 1,1,1,2,2-pentafluoropropionate (for $-CF_2CF_3$), n-butyrate (for $-CH_2-CH_2-CH_3$), n-1,1,1,2,2,3,3-heptafluorobutyrate (for $-CF_2-CF_2-CF_3$), n-valerate (for $-CH_2-CH_2-CH_2-CH_3$) and the corresponding halogenated valerate, etc.. Different types of acylating agents other than the ester, such as the correspondng acid chlorides, anhyrides or amides, may also be used.

As with the nopinato compounds, any of the carbon atoms in the campholyl moiety can be substituted by one or more groups which are not extremely sterically hindered, are not base sensitive, and which do not themselves contain basic groups. Normally substituent groups should contain no carbonyl ester groups, or allylic unsaturation. Preferred substituent groups are lower alkyl or halogenated, preferably fluorinated lower alkyl of 1 to 10, preferably 1 to 4 carbon atoms. Methods of obtaining the desired substituted campholyl compounds are known in the art.

EXAMPLES 5 — 13

Tris [d,d-dicampholylmenthanato] europium (III), the shift reagent of Example 5 in table 1 below, and tris [3-trifluoroacetyl-d-nopinato] europium(III), the shift reagent in Example 6 in table 1 below, were compared in ability to induce enantiomer shift differences in a variety of enantiomeric samples, with a number of other novel shift reagents and a number previously known shift reagents. Identification of the other shift reagents tested, whose preparation is more fully described in McCreary et al. supra, *J. Amer. Chem. Soc.* 96: 1038 (1974), is as follows: the shift reagent in Example 7 is tris [d-campholyl -1- fencholylmethanato] europium(III); the shift reagent in Example 8 is tris [d-campholyl-d-fencholylmethanato] europium(III), the shift reagent in Example 9 is tris [3-(d-fencholyl)-d-camphorato] europium(III); the shift reagent in Example 10 is tris [3-(1-fencholyl)-d-camphorato] europium(III); the shift reagent in Example 11 is tris [3-(tert-butylhydroxymethylene)-d-camphorato] europium(III); the shift reagent in Example 12 is tris [d,1-difencholylmethanato] europium(III); and the shift reagent in Example 13 is tris [3-trifluoroacetyl-d-camphorato] europium(III). Other comparisons with other reagents and under differing conditions are disclosed in McCreary et al., supra.

The NMR spectra were run 60 MHF with a Varian Model T-60 spectrometer or with a Perkin-Elmer Model R-20 spectrometer. All values of the enantiomeric shift difference were measured at 27°C. All spectra were recorded in carbon tetrachloride, except for those of 1-phenylethylamine, sec-butylamine and benzyl methyl sulfoxide, which were obtained using deuterated chloroform. The enantiomeric shift differences obtained are shown in Table 1 below.

TABLE I

| Cmpd | Resonance Observed | EXAMPLE | | | | | | | | |
|---|---|---|---|---|---|---|---|---|---|---|
| | | 5 | 6 | 7 | 8 | 9 | 10 | 11 | 12 | 13 |
| 1-Phenyl- | $CHCH_3$ | 0.66 | 0.21 | 0.60 | 0.62 | 0.27 | 0.10 | 0.21 | 0.12 | 0.50 |
| ethylamine | $CHCH_3$ | 4.42 | 0.10 | 1.30 | 1.65 | 0.10 | 1.13 | 0.55 | 0.10 | |
| | ortho H | 0.15 | 0.12 | 0.13 | 0.13 | 0.13 | 0.0 | 0.13 | 0.00 | 0.05 |
| N-Methyl- | $CHCH_3$ | 0.21 | 0.0 | 0.37 | 0.47 | 0.40 | 0.28 | 0.10 | 0.12 | |
| 1-phenylethyl- | $NCH_3$ | 1.46 | 0.00 | 0.10 | 0.22 | 1.13 | 0.25 | 0.50 | 0.18 | |
| amine | ortho H | 1.45 | 0.0 | 0.30 | 0.43 | 0.23 | 0.14 | 0.09 | 0.00 | |
| N,N Dime- | $CHCH_3$ | 0.26 | 0.7 | 0.13 | 0.23 | 0.05 | 0.03 | | 0.0 | |
| thyl-1-phe- | $N(CH_3)_2$ | 0.85 | 0.15 | 0.17 | 0.43 | 0.17 | 0.24 | 0.05 | 0.0 | |
| nylethyl amine | | | | | | | | | | |
| Sec-butyl- | $CHNH_2$ | 2.93 | 0.0 | 0.57 | 0.75 | 0.20 | 0.30 | | | 0.0 |
| amine | $CHCH_3$ | 0.36 | 0.10 | 0.30 | 0.23 | 0.15 | 0.20 | 0.25 | 0.11 | 0.52 |
| | $CH_2CH_3$ | 0.36 | 0.05 | 0.03 | 0.05 | 0.05 | 0.00 | 0.04 | 0.00 | 0.25 |
| Cyclohexyl- | $CHCH_3$ | 1.22 | 0.50 | 0.10 | 0.10 | 0.08 | 0.09 | 0.00 | 0.03 | 0.07 |
| methylcarbinol | | | | | | | | | | |
| 1-Phenyl- | $CHCH_3$ | 0.70 | 0.55 | 0.23 | 0.25 | 0.0 | 0.0 | 0.00 | 0.1 | 0.30 |
| ethanol | $CHCH_3$ | 0.61 | 0.45 | | 0.00 | 0.02 | 0.10 | 0.00 | 0.0 | 0.00 |
| | ortho H | 0.06 | 0.05 | 0.10 | 0.05 | 0.02 | 0.0 | 0.00 | 0.0 | 0.00 |
| 1,3-Di-tert- | CHOH | 2.50 | 2.02 | | 1.30 | | 1.03 | 0.10 | 0.11 | 0.59 |
| butylpropar- | 1-tert- | 2.43 | 0.48 | | 0.13 | 0.00 | 0.21 | 0.05 | 0.0 | 0.09 |
| gyp alcohol | butyl | | | | | | | | | |
| Benzyl methyl | $CH_3$ | 1.21 | 0.05 | | 0.40 | 0.14 | 0.12 | 0.0 | 0.0 | 0.0 |
| sulfoxide | | | | | | | | | | |
| Sec-butyl | HCO | 0.48 | 0.20 | 0.10 | 0.06 | 0.00 | | 0.0 | 0.03 | 0.0 |
| formate | $CHCH_3$ | 0.40 | 0.06 | 0.10 | 0.10 | 0.00 | | 0.00 | 0.03 | 0.04 |
| | $CH_2CH_3$ | 0.25 | 0.10 | 0.05 | 0.02 | 0.0 | | 0.0 | 0.03 | 0.03 |
| Sec-butyl | HCO | | 0.00 | 0.05 | 0.05 | 0.10 | 0.20 | 0.03 | 0.05 | 0.0 |
| formamide | $CHCH_3$ | 0.30 | 0.00 | 0.05 | 0.09 | 0.05 | 0.03 | 0.05 | 0.05 | 0.10 |
| | $CH_2CH_3$ | 0.22 | 0.02 | 0.05 | 0.04 | 0.02 | 0.02 | 0.03 | 0.05 | 0.05 |
| Camphor | $CH_3$ | 0.12 | 0.10 | 0.00 | 0.00 | 0.04 | | 0.02 | 0.00 | 0.03 |
| | $C(CH_3)_2$ | 0.75 | 0.16 | 0.00 | 0.00 | 0.00 | | 0.00 | 0.00 | 0.12 |
| | | 0.14 | 0.04 | 0.00 | 0.00 | 0.00 | | 0.00 | 0.00 | 0.00 |
| 1-Methoxy-2- | $OCH_4$ | 0.98 | 0.00 | 0.06 | 0.10 | 0.00 | 0.00 | 0.00 | 0.00 | 0.00 |
| methylcyclo- | | 1.02 | 0.2 | 0.07 | 0.17 | 0.01 | 0.02 | 0.01 | 0.00 | 0.00 |
| hexane | | | | | | | | | | |

The specific embodiments described herein are meant to be exemplary only, and various modifications will be apparent to those skilled in the art. The claims below are intended to cover all such modifications as fall within the true spirit and scope of the invention.

We claim:

1. A method of spectral analysis of a composition containing at least one organic compound comprising adding a shift reagent to said composition, said shift reagent being a lanthanide chelate of a ligand selected from d,d-dicampholylmethane, 1,1-dicampholylmethane, and a compound of the formula:

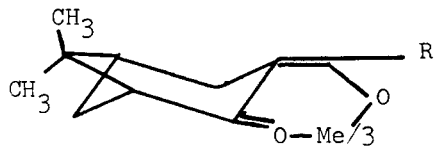

wherein R is hydrogen, alkyl, halogenated alkyl or aryl and Me is a paramagnetic trivalent rare earth ion, and measuring the nuclear magnetic spectrum of said composition containing said shift reagent.

2. The method of claim 1, wherein said shift reagent is a lanthanide chelate of d,d-dicampholylmethane.

3. The method of claim 2, wherein said shift reagent is a lanthanide chelate of 1,1-dicampholylmethane.

4. The method of claim 1, wherein R is selected from hydrogen, lower alkyl, halogenated lower alkyl, and phenyl.

5. The method of claim 1, wherein R is the formula $-C_nF_{2n+1}$, where $n$ is a whole number from 1 to 10.

6. The method of claim 5, wherein $n$ is from 1 to 4.

7. The method of claim 1, wheren said organic compound is an optically active compound.

8. The method of claim 1, wherein said composition contains a mixture of optically active compounds.

9. The method of claim 1, wheren Me is a trivalent europium ion.

* * * * *